United States Patent [19]

Kamachi et al.

[11] Patent Number: 5,194,433
[45] Date of Patent: Mar. 16, 1993

[54] ANTIBIOTIC C-3 CATECHOL-SUBSTITUTED CEPHALOSPORIN COMPOUNDS, COMPOSITIONS AND METHOD OF USE THEREOF

[75] Inventors: Hajime Kamachi, Urayasu; Seiji Iimura, Tokyo, both of Japan

[73] Assignee: Bristol-Myers Squibb Company, New York, N.Y.

[21] Appl. No.: 612,339

[22] Filed: Nov. 13, 1990

[51] Int. Cl.$^5$ .................. C07D 501/38; A61K 31/545
[52] U.S. Cl. ...................................... 514/202; 540/222
[58] Field of Search ................ 514/202; 540/222, 221, 540/225

[56] References Cited

U.S. PATENT DOCUMENTS 4,742,053  5/1988  Nakagawa et al. ................ 540/222
4,814,328  3/1989  Nakagawa et al. ................ 514/205
4,906,623  3/1990  Matsumura et al. ............... 514/202

FOREIGN PATENT DOCUMENTS 2-28186  1/1990  Japan .

Primary Examiner—Nicholas S. Rizzo
Attorney, Agent, or Firm—William T. Han

[57] ABSTRACT

This invention relates to novel antibiotic cephalosporin derivatives of the formula

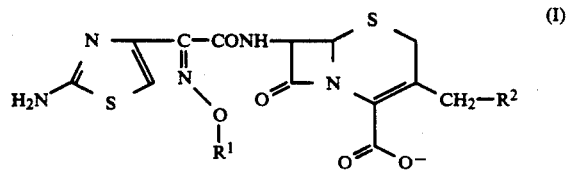

wherein
$R^1$ is hydrogen, $C_{1-6}$ alkyl, $C_{3-6}$ cycloalkyl, or a radical of the formula $$-\underset{R^4}{\overset{R^3}{\underset{|}{\overset{|}{C}}}}-CO_2H$$

in which $R^3$ and $R^4$ are independently hydrogen, methyl or ethyl, or $R^3$ and $R^4$, taken together with the carbon atom to which they are attached, may be a cycloalkylidene ring containing from 3 to 6 carbon atoms;
$R^2$ is a radical selected from the group consisting of

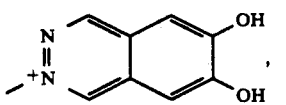

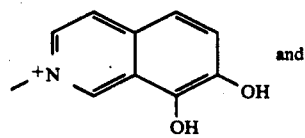

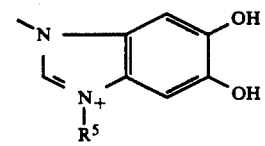

wherein $R^5$ is hydrogen or $C_{1-6}$ alkyl.

This invention further relates to compounds of formula I and their pharmaceutically acceptable salts, physiologically hydrolyzable esters or solvates.

6 Claims, No Drawings

ANTIBIOTIC C-3 CATECHOL-SUBSTITUTED CEPHALOSPORIN COMPOUNDS, COMPOSITIONS AND METHOD OF USE THEREOF

BACKGROUND OF THE INVENTION

The field of this invention is cephalosporins with dihydroxyphenyl (catechol) moieties in the three position, their antibiotic use and compositions thereof.

In the antibiotic arts, there has long been a need for new and effective antibiotic compounds. Due to rapid changes in the pathogens, for which treatment with the antibiotic compounds are required, the older and more used antibiotics often become either ineffective or significantly less effective against the pathogens. Effective antibiotics are therefore in constant demand to replace the older and more used antibiotics. Accordingly, a great many cephalosporin compounds have been synthesized and tested for appropriate antibiotic properties by those in the antibiotic field. Because of the above mentioned long felt need in this art for potent and effective antibiotics, even small improvements or advancements in the art can sometimes be very significant.

DESCRIPTION OF RELATED ART

A number of cephalosporin compounds, having a catechol moiety in the three position have been evaluated for antibiotic properties by those in the art. Patents and printed publications which disclose related arts of the present invention are as follows:

(A) U.S. Pat. No. 4,814,328 (issued on Mar. 21, 1989 to Nakagawa, et al.) discloses, inter alia, cephalosporins of the formula

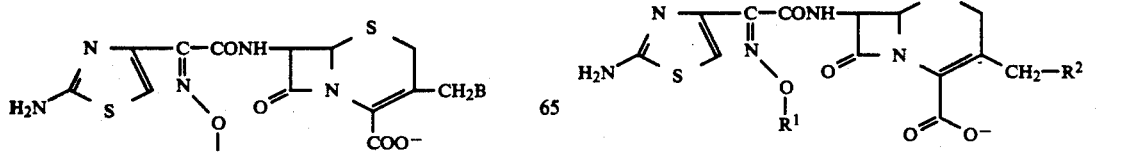

in which A is a straight or branched lower alkyl group which may be substituted by a carboxy group; and B is a radical of the formula

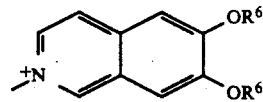

in which $R^6$ equals hydrogen or acetyl.

(B) Japan Kokai 2-28186 (published on Jan. 30, 1990) discloses, inter alia, cephalosporins of the formula

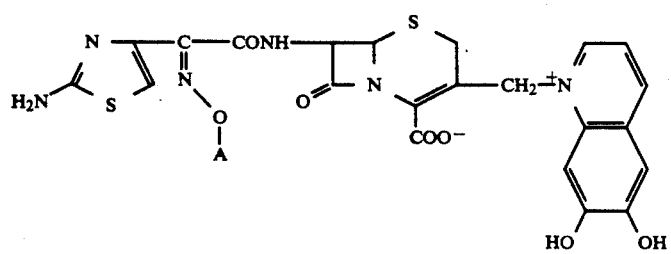

wherein A is hydrogen, lower alkyl, cycloalkyl, lower alkenyl, lower alkynyl, aryl or aralkyl and each may subtituted.

(C) U.S. Pat. No. 4,906,623 (issued on Mar. 6, 1990 to Matsumura et al.) discloses, inter alia, compounds of the formula

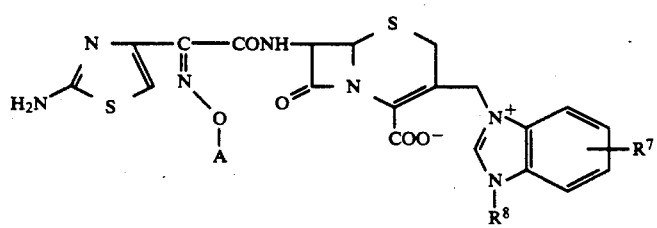

in which $R^7$ is hydroxy, $R^8$ is hydrogen or $C_{1-12}$ alkyl, and A is hydrogen, $C_{1-6}$ aklyl, or a radical of the formula

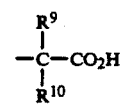

wherein $R^9$ and $R^{10}$ are independently hydrogen, methyl or ethyl.

SUMMARY OF THE INVENTION

This invention relates to novel cephalosporin derivatives of the formula (I)

wherein $R^1$ is hydrogen, $C_{1-6}$ alkyl, $C_{3-6}$ cycloalkyl, or a radical of the formula

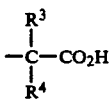

in which $R^3$ and $R^4$ are independently hydrogen, methyl or ethyl, or $R^3$ and $R^4$, taken together with the carbon atom to which they are attached, may be a cycloalkylidene ring containing from 3 to 6 carbon atoms;

$R^2$ is a radical selected from the group consisting of

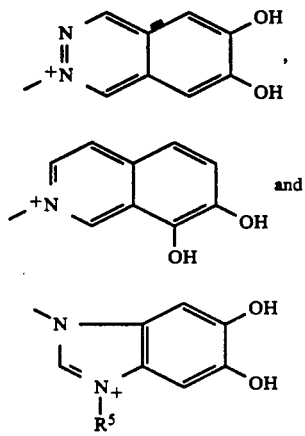

wherein $R^5$ is hydrogen or $C_{1-6}$ alkyl.

This invention further relates to compounds of formula I and their pharmaceutically acceptable salts, physiologically hydrolyzable esters or solvates.

Representative compounds of this invention were selected for testing and were shown to display potent antibacterial activity. Thus, as another aspect of the invention, a compound of the series can be incorporated into pharmaceutical compositions for use in mammals, especially in human patients, afflicted with bacterial infections.

DESCRIPTION OF THE INVENTION

As shown in formula I below, the numbering system used for the cephalosporins of the present specification follows the most widely used system in the art.

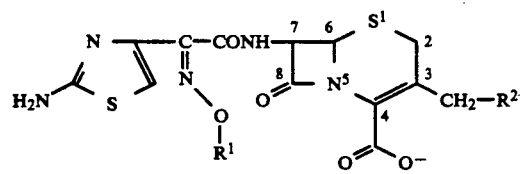

The imino groups in the C-7 side chains of formula I compounds have either the "syn" (Z) or the "anti" (E) configuration. Formula I is drawn as the "syn" isomer. This invention comprises compounds of formula I containing at least 90% of the "syn" isomer. Preferably the compounds of formula I are "syn" isomers which are essentially free of the corresponding "anti" isomers.

In the above definition of the compounds represented by formula I, $C_{1-6}$ alkyl refers to straight or branched chain alkyl groups such as methyl, ethyl, n-propyl, isopropyl, n-butyl, t-butyl, n-pentyl, n-hexyl, 3-methylpentyl, and like alkyl groups; $C_{3-6}$ cycloalkyl refers to groups such as cyclopropyl, cylcopentyl, cyclohexyl, 2-methylpropyl, 2-methylpentyl, and the like groups.

All structural formulas as drawn herein are believed to best represent the structures of the compounds. Some compounds within the scope of the formula I may exist as other tautomeric forms, in which hydrogen atoms are transposed to other parts of the molecules and the chemical bonds between the atoms of the molecules are consequently rearranged. The structural formula I is intended to represent and include such tautomeric forms, insofar as they may exist.

The physiologically hydrolyzable esters serve as prodrugs by being hydrolyzed in the body to yield the antibiotic per se. They are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$ alkyl, benzyl, 4-methoxybenzyl, indanyl, phthalidyl, methoxymethyl, $C_{1-6}$ alkanoyloxy($C_{1-6}$)alkyl, e.g. acetoxymethyl, pivaloyloxymethyl or propionyloxymethyl, $C_{1-6}$ alkoxycarbonyloxy($C_{1-6}$)alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)methyl and other physiologically hydrolyzable esters known and used in the penicillin and cephalosporin arts. Such esters are prepared by conventional techniques known in the art.

The compounds of formula I may form pharmaceutically acceptable salts in the form of acid addition salts, metal and amine salts, or by themselves in the zwitterionic forms.

The pharmaceutically acceptable acid addition salts of formula I compounds are those in which anion does not contribute significantly to the toxicity of the salt and are compatible with the customary pharmaceutical vehicles and adapted for oral or parenteral adimistration. The pharmaceutically acceptable acid addition salts include the salts of compounds of formula I with mineral acids such as hydrochloric acid, hydrobromic acid, phosphoric acid and sulfuric acid, with organic carboxylic acids or organic sulfonic acids such as acetic acid, citric acid, maleic acid, succinic acid, benzoic acid, tartaric acid, fumaric acid, mandelic acid, ascorbic acid, malic acid, methanesulfonic acid, p-tolenesulfonic acid and other acids known and used in the penicillin and cephalosporin arts. Preparation of these salts is carried out by conventional techniques involving reaction of compounds of formula I with the acid in a substantially equivalent amount.

Compounds of formula I may also form pharmaceutically acceptable metal and amine salts in which the cation does not contribute significantly to the toxicity or biological activity of the salt. These salts are also part of the present invention. Suitable metal salts include the sodium, potassium, calcium, barium, zinc and aluminum salts. The sodium or potassium salts are preferred. Amine salts prepared from amines used, for instance, with benzyl penicillin which are capable of forming stable salts with the acidic carboxy group include trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine and dicyclohexylamine.

Compounds of formula I exhibit high antibacterial activity against various Gram-positive and Gram-negative bacteria, and are useful in the treatment of bacterial infections in animals, including man. Compounds of formula I may be formulated for parenteral use in a conventional manner utilizing known pharmaceutical carriers and excipients, and may be presented in unit dosage form or in multidosage containers. The compositions may be in the form of solutions, suspensions or emulsions in oily or aqueous vehicles, and may contain conventional dispersing, suspending or stabilizing agents. The compositions may also be in the form of a dry powder for reconstitution before use, e.g. with sterile, pyrogen-free water. Compounds of formula I may also be formulated as suppositories utilizing conventional suppository bases such as cocoa butter or other glycerides. The compounds of this invention may, if desired, be administered in combination with other antibiotics such as penicillins or other cephalosporins.

When provided in unit dosage forms the compositions will preferably contain from about 50 to about 1500 mg of the active ingredient of formula I. The dosage of the compounds of formula I is dependent on such factors as the weight and age of the patient as well as the particular nature and severity of the disease, and is within the discretion of the physician. However, the dosage for adult human treatment will usually be in the range of from about 500 to about 5000 mg per day, depending on the frequency and route of administration. When administered intramuscularly or intravenously to an adult human, a total dosage of from about 750 to about 3000 mg per day, in divided doses, normally will be sufficient, although higher daily doses of some of the compounds may be desirable in the case of Pseudomonas infections.

The compounds of the present invention can be synthesized by a process depicted in Scheme I. In the scheme $R^{12}$ and $R^{13}$ are conventional carboxy and amino protecting groups, respectively; and $R^{11}$ is a conventional hydroxy protecting group, $C_{1-6}$ alkyl, $C_{3-6}$ cycloalkyl, or a radical of the formula

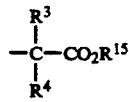

in which $R^3$ and $R^4$ are independently hydrogen, methyl or ethyl, or $R^3$ and $R^4$, taken together with the carbon atom to which they are attached, may be a cycloalkylidene ring containing from 3 to 6 carbon atoms; and $R^{15}$ is a conventional carboxy protecting group which may or may not be the same as $R^{12}$.

SCHEME I

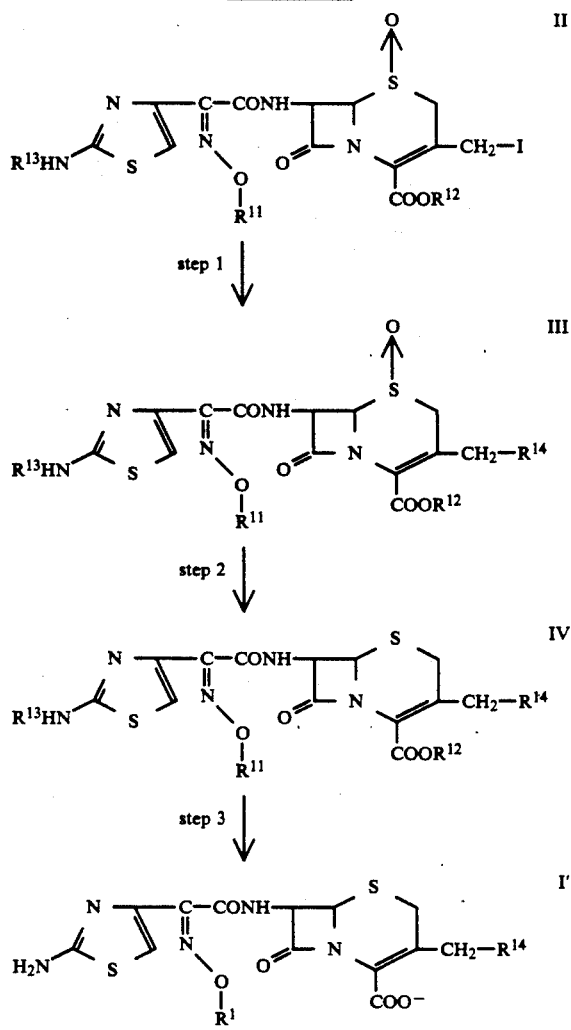

In step 1, a sulfoxide of formula II is treated with an amine selected from the group

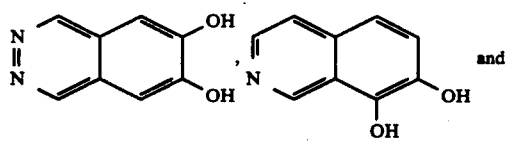

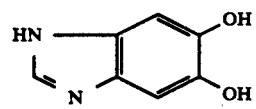

to afford a compound of formula III in which $R^{14}$ is a radical from the group

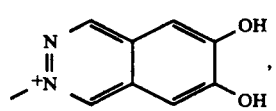

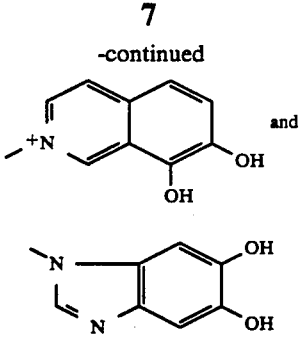

This substitution process can be carried out in any inert organic solvent, preferably in a polar solvent such as dimethylformamide. The temperature range of the reaction can be between 0° C. to the boiling point of the solvent being used, but it can be more conveniently carried out at room temperature. In step 2, the sulfoxide group in a compound of formula III is reduced. The reagents such as acetyl chloride and potassium iodide in acetone or phosphorus tribromide in dimethylformamide is typically employed. Finally in step 3, protecting group(s) are removed to afford a compound within the scope of this invention.

When a compound of formula IV has $R^{14}$ as the radical of the formula,

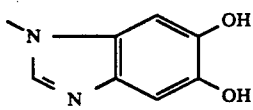

it can be treated with $R^5X$ to afford a compound of formula IV' from which protecting groups are removed to afford additional compounds of the present invention. The radical X refers to a leaving group such as chloro, bromo, iodo, and the like groups.

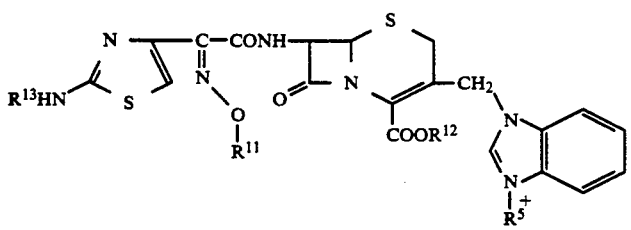

As used herein, conventional carboxy protecting groups which can be employed in the present invention to block or protect the carboxylic acid function are well-known to those skilled in the art and, preferably, said group(s) can be removed, if desired, by methods which do not result in any appreciable destruction of the remaining portion of the molecule, for example, by chemical or enzymatic hydrolysis, treatment with chemical reducing agents under mild conditions, irradiation with ultraviolet light or catalytic hydrogenation. Examples of such readily removable carboxy-protecting groups include moieties such as $C_{1-6}$ alkyl, diphenylmethyl (benzhydryl), 2-naphthylmethyl, 4-pyridylmethyl, phenacyl, acetonyl, 2,2,2-trichloroethyl, silyl such as trimethylsilyl and t-butyldimethylsilyl, phenyl, ring substituted phenyl, e.g., 4-chlorophenyl, tolyl, and t-butylphenyl, phenyl $C_{1-6}$ alkyl, ring substituted phenyl $C_{1-6}$ alkyl, e.g., benzyl, 4-methoxybenzyl, 4-nitrobenzyl (p-nitrobenzyl), 2-nitrobenzyl (o-nitrobenzyl), and triphenylmethyl (trityl), methoxymethyl, 2,2,2-trichloroethoxycarbonyl, benzyloxymethyl, $C_{1-6}$ alkanoyloxy $C_{1-6}$ alkyl such as acetoxymethyl, propionyloxymethyl, $C_{2-6}$ alkenyl such as vinyl and allyl. Other suitable carboxy protecting groups well known in the art but have not been disclosed above can be found in "Protective Groups in Organic Synthesis", Theodora W. Greene (John Wiley & Sons, 1981), Chapter 5. Particularly advantageous carboxy protecting groups are benzyl, p-nitrobenzyl, o-nitrobenzyl, 2,4-dimethoxybenzyl, 4-methoxybenzyl, allyl, substituted allyl, t-butyl or diphenylmethyl (DPM).

Conventional amino protecting groups are also well-known to those skilled in the art and have reference to groups commonly employed in protecting or blocking the amino functional group during a reaction step and which can be split off subsequently without destroying or substantially destroying the remaining portion of the molecule. Examples include vinyl, allyl, t-butoxycarbonyl, benzyl, benzyloxycarbonyl, 2-nitrobenzyl, 4-nitrobenzyl, 2-nitrobenzyloxylcarbonyl, formyl, benzoyl, acetyl, ethylcarbonyl, chloroacetyl, trichloroacetyl, trifluoroacetyl, methyloxycarbonyl, allyloxycarbonyl, trimethylsilyl, triethylsilyl, triphenylsilyl, t-butyldimethylsilyl, methyldiphenylsilyl, 2,4-dimethoxybenzyl, 2,4-dimethoxybenzyloxycarbonyl, 4-methoxybenzyl, 4-(methoxymethyloxy)phenyl, bis(4-methoxyphenyl)-methyl, t-butoxycarbonylmethyl, allyoxycarbonylmethyl, methoxymethyl, methylthiomethyl, methoxyethoxymethyl, [2-(trimethylsilyl)ethoxy]methyl or 2-(methylthiomethoxy)ethoxycarbonyl. In general, amino protecting groups which are readily removed under acid conditions or catalytic hydrogenolysis are preferred, e.g. t-butoxycarbonyl, benzyloxycarbonyl and triphenylmethyl. Other suitable amino protecting groups well known to those skilled in the art can be found in "Protective Groups in Organic Synthesis", Theodora W. Greene (John Wiley & Sons, 1981), Chapter 7.

Conventional hydroxy protecting groups represents a group commonly employed in protecting the hydroxy group during a reaction step and which can be split off subsequently without destroying or substantially destroying the remaining portion of the molecule. Examples include triphenylmethyl, trimethylsilyl, triethylsilyl, triisopropylsilyl, t-butyldimethylsilyl, triphenylsilyl, trimethylsilylethoxycarbonyl, benzyl, benzyloxycarbonyl, 2-nitrobenzyl, 4-nitrobenzyl, 2-nitrobenzyloxycarbonyl, 4-nitrobenzyloxycarbonyl, t-butyloxycarbonyl, allyloxycarbonyl, 4-methoxybenzylcarbonyl, formyl, acetyl, trichloroacetyl, 2,2,2-trichloroethoxycarbonyl, 2,4-dimethoxybenzyl, 2,4-dimethoxybenzyloxycarbonyl, methoxymethyl, methylthiomethyl, methoxyethoxymethyl, [2-(trimethylsilyl)ethoxy]methyl, 2-(methylthiomethoxy)ethoxycarbonyl, tetrahydropyranyl or benzoyl. Other conventional hydroxy protecting groups can be found in "Protective Groups in Organic Synthesis", Theodora W. Greene (John Wiley & Sons, 1981), Chapter 2.

DESCRIPTION OF SPECIFIC EMBODIMENTS

The specific examples which follow illustrate the synthesis of representative compounds of the instant invention and are not construed as limiting the invention in sphere or scope. The methods may be adopted to variations in order to produce compounds embraced by this invention but not specifically disclosed. Further, variations of the methods to produce the same compounds in somewhat different fashion will also be evident to one skilled in the art.

All temperatures are understood to be in Centigrade (C) when not specified. The nuclear magnetic resonance (NMR) spectral characteristics refer to chemical shifts ($\delta$) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiplet (m), doublet (d), quartet (q), triplet (t), doublet of doublet (dd), doublet of triplet (dt), and doublet of quartet (dq). The solvents employed for taking NMR spectra are DMSO-$d_6$ (perdeuterodimethysulfoxide), $D_2O$ (deuterated water), $CDCl_3$ (deuterochloroform) and other conventional deuterated solvents. The infrared (IR) spectral description include only absorption wave numbers ($cm^{-1}$) having functional group identification value.

EXAMPLE 1

Diphenylmethyl 7-[(Z)-2-(2-tritylaminothiaminothiaxol-4-yl)-2-(1-t-butoxycarbonyl-1-methylethoxyimino)acetamido]-3-(5,6-dihydroxybenzimidazol-1-yl)methyl-3-cephem-4-carboxylate 1-oxide (IIIa)

5,6-Dihydroxybenzimidazole (147 mg, 0.98 mmol) was added to a solution of diphenylmethyl 7-[(Z)-2-(2-tritylaminothiazol-4-yl)-2-(1-t-butoxycarbonyl-1-methylethoxyimino)acetamido]-3-iodomethyl-3-cephem-4-carboxylate 1-oxide (IIa) (774 mg, 0.72 μmmol) in DMF (3 ml). The mixture was stirred for 1 hr at room temperature, poured into cold water and extracted with EtOAc. The extracts were washed with water and evaporated under reduced pressure to give 860 mg of the title product.

IR $\nu_{max}$ (KBr) $cm^{-1}$ 1795, 1720, 1680; MP 185° C. (dec); Mass (FAB), m/z 1098 (M+H)+

EXAMPLE 2

Diphenylmethyl 7-[(Z)-2-(2-tritylaminothiazol-4-yl)-2-(1-t-butoxycarbonyl-1-methylethoxyimino)acetamido]-3-(5,6-dihydroxybenzimidazol-1-yl)methyl-3-cephem-4-carboxylate (IVa)

Acetyl chloride (275 mg) was added to a mixture of compound IIIa (1.1 g, 1 mmol) and KI (1.0 g) in acetone (20 ml) at 0° C. for 30 min. An additional amount of KI (1.0 g) and acetyl chloride (275 mg) was added. The mixture was stirred for additional 30 min at the same temperature. The mixture was poured into cold 10% sodium pyrosulfate and extracted with EtOAc. The extract was washed with water, dried and concentrated in vacuo. Trituration of the residue with ether gave 1.03 g of the title product, contaminated with some O-acetylated products.

IR $\nu_{max}$ (KBr) $cm^{-1}$ 1780, 1710, 1670.

EXAMPLE 3

7-[(Z)-2-(2-Aminothiazol-4-yl)-2-(1-carboxy-1-methylethoxyimino) acetamido]-3-(5,6-dihydroxybenzimidazol-1-yl)methyl-3-cephem-4-carboxylic acid (Ia)

A mixture of compound IVa (500 mg) and anisole (0.5 ml) in trifluoroacetic acid (2 ml) was stirred for 1 hr at room temperature and concentrated in vacuo. The residue was triturated with isopropyl ether to give 382 mg of trifluoroacetate of the crude product, which was chromatographed on a column of Prep $C_{18}$ (20×300 mm). The column was eluted with water containing 15% MeOH. The fractions containing the desired product were combined and concentrated in vacuo and the aqueous residue was freeze-dried to give 34 mg of the product. Physicochemical data of the product is shown in Table 1 and Table 2.

EXAMPLE 4

A. 7,8-Dihydroxyisoquinoline hydrobromide 7,8-Dimethoxyisoquinoline (3.2 g, 16.9 mmol) in a mixture of 47% HBr (30 ml) and acetic acid (30 ml) was heated under reflux overnight. After cooling the product crystallized out from the reaction mixture as yellow needles. The crystals were collected by filtration to yield 2.5 g (Yield 61%) of the HBr salt. MP 243°-14 245° C.;

IR $\nu_{max}$ $cm^{-1}$ 1620, 1570, 1535, 1505; $^1$H NMR (DMSO-$d_6$) $\delta$ ppm 9.32 (1 H, s, 1—H), 8.20 (1 H, d, J=6 Hz), 7.1–7.7 (3 H, m).

Anal. Calcd for $C_9H_8NO_2Br.1/2H_2O$: C 43.05, H 3.69, N 5.58, Br 31.82.

Found: C 43.06, H 3.61, N 5.58, Br 31.70.

B. Preparation of the free base

A solution of the above hydrobromide (1.0 g, 4.0 mmol) in water was adjusted to pH 7 with sodium bicarbonate and the resulting precipitate was collected by filtration to yield 0.74 g (Yield, quantitative).

IR $\nu_{max}$ (KBr) $cm^{-1}$ 1630, 1590, 1570.

EXAMPLE 5

Diphenylmethyl 7-[((Z)-2-(2-tritylaminothiazol-4-yl)-2-(1-t-butoxycarbonyl-1-methylethoxyimino)acetamido]-3-(2.8-dihydro-7-hydroxy-8-oxoisoquinolin-2-yl)methyl-3-cephem-4-carboxylate 1-oxide (IIIb)

A mixture of diphenylmethyl 7-[(Z)-2-(2-tritylaminothiazo-4-yl)-2-(1-t-butoxycarbonyl-1-methylethoxyimino)acetamido]-3-iodomethyl-3-cephem-4-carboxylate 1-oxide (IIa) (538 mg, 0.5 mmol) and 7,8-dihydroxyisoquinoline (121 mg, 0.75 mmol) in DMF (5 ml) was stirred at room temperature for 1 hr. The reaction mixture was diluted with EtOAc (100 ml), washed with aqueous sodium thiosulfate, water, and aqueous sodium chloride, dried over magnesium sulfate and concentrated to yield 533 mg (Yield, 98%) of the title compound.

IR $\nu_{max}$ (KBr) $cm^{-1}$ 1790, 1720, 1680.

EXAMPLE 6

7-[(Z)-2-(2-Aminothiazol-4-yl)-2-(1-carboxy-1-methylethoxyimino)acetamido]-3-(2,8-dihydro-7-hydroxy-8-oxo-isoquinolin-2-yl)methyl-3-cephem-4-carboxylic acid (Ib)

To a solution of compound IIIb (425 mg, 0.39 mmol) in DMF (1 ml) was added phosphorus tribromide (0.037 ml, 0.39 mmol) at 0° C. The mixture was stirred for 1 hr at room temperature. Additional phosphorus tribromide (0.037 ml, 0.39 mmol) was added to the reaction mixture and the whole mixture was stirred at room temperature for an additional 1 hr. The reaction mixture was diluted with EtOAc, washed with aqueous sodium bicarbonate, water, and aqueous sodium chloride, dried over magnesium sulfate and concentrated under reduced pressure. The residue was treated with trifluoroacetic acid (1 ml) at room temperature for 1 hr and diluted with isopropyl ether to afford 183 mg of the crude product which was subjected to Prep $C_{18}$ column chromatography eluted with 20% acetonitrile-water. The desired fractions, as determined by HPLC, were combined and concentrated to a small volume and lyophilized to yield 16 mg (Yield 7%) of the title compound. Physicochemical data of the product is shown in Tables 1 and 2.

EXAMPLE 7

6,7-Dihydroxyohthalazine hydrobromide 6,7-Dimethoxyphthalazine (900 mg, 4.74 mmol) in a mixture of 47% HBr (9 ml) and acetic acid (9 ml) was heated under reflux overnight. After cooling the product crystallized out from the reaction mixture as colorless crystals. The crystals were collected by filtration to yield 524 mg (Yield 47%) as the HBr salt. MP >260° C. (gradual decomposition);

IR $\nu_{max}$cm$^{-1}$ 1610, 1580, 1520, 1500;

$^1$H NMR (DMSO-d$_6$) δ ppm 9.82 (2 H, s), 7.25 (2 H, s).

Anal. Calcd for $C_8H_7N_2O_2Br$: C 39.53, H 2.90, N 11.53, Br 32.87

Found: C 39.44, H 2.86, N 11.14, Br 33.12.

EXAMPLE 8

Diphenylmethyl 7-[(Z)-2-(2-tritylaminothiazol-4-yl)-2-(1-t-butoxycarbonyl-1-methylethoxyimino)acetamido]-3-(2,6-dihydro-7-hydroxy-6-oxophthalazin-2-yl)methyl-3-cephem-4-carboxylate 1-oxide (IIIc)

A mixture of diphenylmethyl 7-[(Z)-2-(2-tritylaminothiazol-4-yl)-2-(1-t-butoxycarbonyl-1-methylethoxyimino)acetamido]-3-iodomethyl-3-cephem-4-carboxylate 1-oxide (IIa, 538 mg, 0.5 mmol), 6,7-dihydroxyphthalazine hydrobromide (158 mg, 0.65 mmol) and triethylamine (0.1 ml, 0.7 mmol) in DMF (1.5 ml) was stirred at room temperature for 3 hr. The reaction mixture was diluted with EtOAc (100 ml), washed with aqueous sodium thiosulfate, water, and aqueous sodium chloride, dried over magnesium sulfate and concentrated to yield 547 mg of a crude product, which was chromatographed on a silica gel column (7 g, 5% methanol in chloroform). The desired fractions were combined and concentrated to yield 532 mg (Yield 97%) of the title compound.

IR $\nu_{max}$ (KBr) cm$^{-1}$ 1790, 1720, 1680;

Mass (FAB) m/z 1110 (M+H)$^+$.

EXAMPLE 9

Diphenylmethyl 7-[(Z)-2-(2-tritylaminothiazol-4-yl)-2-(1-t-butoxycarbonyl-1-methylethoxyimino)acetamido]-3-(2,6-dihydro-7-hydroxy-6-oxophthalazin-2-yl)methyl-3-cephem-4-carboxylate (IVb)

To a solution of compound IIIc (510 mg, 0.46 mmol) in DMF (1 ml) was added phosphorus tribromide (0.051 ml, 0.54 mmol) at −10° C. The mixture was stirred for 2 hr at the same temperature. The reaction mixture was diluted with ethyl acetate, washed with aqueous sodium bicarbonate, water, and aqueous sodium chloride, dried over magnesium sulfate and concentrated under reduced pressure. The resulting residue was chromatographed on a silica gel column (4 g, 1% methanol in chloroform) to afford 149 mg (Yield 30%) of the title compound.

IR $\nu_{max}$ (KBr) cm$^{-1}$ 1780, 1720, 1670;

Mass (FAB) m/z 1094 (M)$^+$.

EXAMPLE 10

7-[(Z)-2-(2-Aminothiazol-4-yl)-2-(1-carboxy-1methylethoxyimino)acetamido]-3-(2,6-dihydro-7-hydroxy-6-oxophthalazin-2-yl)methyl-3-cephem-4-carboxylic acid (Ic)

Compound IVb (145 mg, 0.13 mmole) was treated with trifluoroacetic acid (1 ml) at room temperature for 1 hr and diluted with isopropyl ether to afford 95 mg of a crude product which was subjected to a Prep $C_{18}$ column eluted with 10% acetonitrile. The desired fractions, as determined by HPLC, were combined, concentrated to a small volume and lyophilized to yield 28 mg (Yield 34%) of the title compound. Physicochemical data of the product is shown in Table 1 and Table 2.

EXAMPLE 11

7-[(Z)-2-(2-Aminothiazol-4-yl)-2-(1-carboxy-1-methylethoxyimino)acetamido]-3-(5,6-dihydroxy-3-methylbenzimidazol-3-io-1-yl)methyl-3-cephem-4-carboxylate (Id)

The dihydroxybenzimidazole derivative obtained in Example 2 (620 mg, 0.57 mmol) was dissolved in methyl iodide (8 ml) and the mixture was stirred for 8 hr at room temperature and concentrated in vacuo to give 800 mg of diphenylmethyl 7-[(Z)-2-(2-tritylaminothiazol-4-yl)-2-(1-t-butoxycarbonyl-1-methylethoxyimino)acetamido]-3-(5,6-dihydroxy-3-methylbenzimidazol-3-io-1-yl)methyl-3-cephem-4-carboxylate (Va). A mixture of compound Va (800 mg) and anisole (0.3 ml) in trifluoroacetic acid (3 ml) was stirred for 1 hr at room temperature and concentrated in vacuo. The resulting residue was triturated with isopropyl ether to give 457 mg of crude trifluoroacetate salt of the title product, which was chromatographed on a column of Prep $C_{18}$ (20×300 mm). The column was eluted with water containing 0–25% acetonitrile. The fractions containing the desired product were combined and concentrated in vacuo. The concentrate was freeze-dried to give 135 mg of the desired product containing a small amount O -acetylated by-products. To a solution of the product in pH 7 phosphate buffer (12 ml) was added acetylesterase (Sigma 1.0 ml). The mixture was stirred at room temperature for 30 min during which period it was kept at pH 7.0 by the addition of NaHCO$_3$ and citric acid. The mixture was acidified by the addition of dilute HCl and chromatographed on a column of HP-20 (40 ml). After elution with water, the column was eluted with MeOH and the eluate was fractionated. The desired fractions were combined and concentrated in vacuo. The resulting residue was chromatographed again on a column of Prep $C_{18}$ (20×300 mm). The column was eluted with water containing 0-25% acetonitrile. The fractions containing the desired product were combined and concentrated in vacuo. Freeze-drying of the residue gave 22 mg of the title compound as amorphous powder. Physicochemical data of the product is shown in Table 1 and Table 2.

TABLE 1

IR, UV and Mass spectra and Mp of Ia, Ib, Ic and Id

| Compound | IR (KBr, cm$^{-1}$) | UV (pH 7 buffer, nm ($\epsilon$)) | MASS (FAB, m/z) | MP °C. (dec.) |
|---|---|---|---|---|
| Ia | 1760, 1620 | 256 (18300) 262 (17700) 295 (13200) | 618 (M + H)$^+$ | 200 |
| Ib | 1760, 1630 | 272 (16900) 330 (sh, 29000) | 629 (M + H)$^+$ | >200 |
| Ic | 1770, 1620 | 250 (sh, 29000) 270 (36000) | 630 (M + H)$^+$ | >150 |
| Id | 1760, 1590 | 255 (sh, 17300) 297 (14200) | 632 (M + H)$^+$ | >180 |

TABLE 2

$^1$H NMR spectra of Ia, Ib, Ic and Id (in ppm, $D_2O$ + $NaHCO_3$)

| Group | Ia | Ib | Ic | Id |
|---|---|---|---|---|
| $CH_3$ (s) | 1.47 | 1.47 | 1.47 | 1.46 |
| $CH_3$ (s) | 1.49 | 1.48 | 1.48 | 1.47 |
| 2-H (d, J=18 Hz) | 3.17 | 3.27 | 3.44 | 3.20 |
| 2-H (d, J=18 Hz) | 3.26 | 3.57 | 3.60 | 3.48 |
| 3'-H (d, J=15 Hz) | 5.10 | 5.36 | 5.35 | 5.18 |
| 3'-H (d, J=15 Hz) | 5.28 | 5.41 | 5.43 | 5.26 |
| 6-H (d, J=5 Hz) | 5.17 | 5.29 | 5.25 | 5.22 |
| 7-H (d, J=5 Hz) | 5.82 | 5.89 | 5.86 | 5.83 |
| thiazole (s) | 6.98 | 6.99 | 6.98 | 6.95 |
| | 7.17 | 7.11 | 7.08 | 3.95 (3H, s) |
| | (1H, s) | (1H, d, J=8.4 Hz) | (1H, s) | |
| heterocyclic catechol moiety | 7.22 (1H, s) | 7.66 (1H, d, J=8.4 Hz) | 7.38 (1H, s) | 7.11 (1H, s) |
| | 8.35 | 7.92 | 8.95 | 7.18 |
| | (1H, s) | (2H, m) 9.42 (1H, s) | (1H, s) 9.25 (1H, s) | (1H, s) 8.92 (1H, s) |

BIOLOGICAL ACTIVITY

Table 3 lists the in vitro antibacterial activity of several representative compounds of the invention. The activity has been evaluated in terms of minimum inhibitory concentrations (MIC's) by a standard two-fold serial agar dilution method in Mueller-Hinton agar. The values are in geometric means of MIC's against the strains tested in each group. The activity of the known compound ceftazidime is also given for comparison.

TABLE 3

In vitro activity of the cephalosporins
Geometric mean of MIC (μg/ml)

| Compound | Gp-Ia (5)* | Gp-Ib (5) | Gn-Ia (5) | Gn-Ib (5) | Gn-II (5) | Pa (S) (10) | Pa (MR) (8) | Pa (HR) (8) | Xm (4) | Pc (2) |
|---|---|---|---|---|---|---|---|---|---|---|
| Ia | 50 | 50 | 0.61 | 0.80 | 1.6 | 0.14 | 0.47 | 0.37 | 3.1 | 12.5 |
| Ib | 100 | >100 | 0.60 | 0.80 | 2.4 | 1.2 | 2.9 | 2.6 | 12.5 | 8.9 |
| Ic | 25 | 33 | 0.11 | 0.033 | 0.40 | 0.033 | 0.37 | 0.73 | 6.3 | 0.57 |
| Id | 25 | 33 | 0.044 | 0.15 | 0.15 | 0.057 | 0.31 | 0.18 | 0.80 | 3.2 |
| ceftazidime | 6.3 | 12.5 | 0.17 | 0.30 | 0.91 | 1.2 | 14 | 65 | 71 | 18 |

*: Number of strains tested
Gp-Ia: Penicillin (PC)-sensitive S. aureus
Gp-Ib: PC-resistant S. aureus
Gn-Ia: Cephalothin (CET)-sensitive E. coli (2 strains), Kl. pneumoniae (1) and Pr. mirabilis (2)
Gn-Ib: CET-sensitive E. coli (3) and Kl. pneumoniae (2)
Gn-II: M. morganii (1), Ent. cloacae (2) and Ser. marcesens (2)
Pa (S): Ceftazidime-sensitive P. aeruginosa
Pa (MR): Ceftazidime-moderately resistant P. aeruginosa
Pa (HR): Ceftazidime-highly resistant P. aeruginosa
Xm: X. moltophilia
Pc: P. cepacia

What is claimed is:

1. A compound of the formula (I)

[structure of cephalosporin compound with thiazole, oxime ether, and β-lactam moieties, showing $H_2N$, S, N, $R^1$, CONH, O, N, $CH_2-R^2$, $O^-$ groups]

wherein
$R^1$ is hydrogen, $C_{1-6}$ alkyl, $C_{3-6}$ cycloalkyl, or a radical of the formula

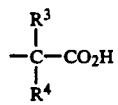

in which $R^3$ and $R^4$ are independently hydrogen, methyl or ethyl, or $R^3$ and $R^4$, taken together with the carbon atom to which they are attached, may be a cycloalkylidene ring containing from 3 to 6 carbon atoms;

$R^2$ is a radical of the formula

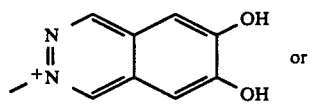 or

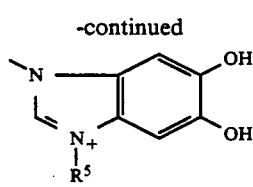

wherein $R^5$ is hydrogen or $C_{1-6}$ alkyl; or a pharmaceutically acceptable salt, physiologically hydrolyzable ester or solvate thereof.

2. The compound of claim 1 which is 7-[(Z)-2(2-aminothiaxol-4-yl)-2-(1-carboxyl-1-methylethoxyimino)acetamido]-3-(5,6-dihydroxybenzimidazol-1-yl)methyl-3-cephem-4-carboxylic acid.

3. The compound of claim 1 which is 7-[(Z)-2(2-aminothiaxol-4-yl).    -2-(1-carboxy-1-methylethoxyimino)acetamido]-3-(2,6-dihydro-7-hydroxy-6-oxophthalazin-2-yl)methyl-3-cephem-4-carboxylic acid.

4. The compound of claim 1 which is 7-[(Z)-2(2-aminothiaxol-4-yl)-2-(1-carboxy-1-methylethoxyimino)acetamido]-3-(5,6-dihydroxy-3-methylbenzimidazol-3-io-1-yl)methyl-3-cephem-4-carboxylate.

5. A method for treating bacterial infection in a mammal, which comprises administering to said mammal an antibacterial effective amount of a compound of claim 1.

6. A pharmaceutical composition comprising an antibacterial effective amount of claim 1 and a pharmaceutically acceptable carrier or diluent.

* * * * *